United States Patent [19]
Christopher

[11] Patent Number: 5,694,929
[45] Date of Patent: Dec. 9, 1997

[54] METHOD AND APPARATUS FOR VENTILATION/OXYGENATION DURING GUIDED INSERTION OF AN ENDOTRACHEAL TUBE

[76] Inventor: Kent L. Christopher, 9086 E. Colorado Cir., Denver, Colo. 80231

[21] Appl. No.: 607,332

[22] Filed: Feb. 26, 1996

[51] Int. Cl.⁶ .................................................. A61M 16/00
[52] U.S. Cl. .............................. 128/207.14; 128/207.15; 128/205.25; 128/911; 128/912; 128/206.29; 128/206.28
[58] Field of Search ..................... 128/202.27, 207.14, 128/206.26, 207.15, 205.25, 911, 912, 203.29, 206.29, 206.28, 207.17, 205.26, 203.21, 205.21

[56] References Cited

U.S. PATENT DOCUMENTS

| | | | |
|---|---|---|---|
| 3,683,908 | 8/1972 | Michael et al. | 128/200.26 |
| 3,809,079 | 5/1974 | Buttaravoli. | |
| 4,054,135 | 10/1977 | Berman. | |
| 4,067,331 | 1/1978 | Berman. | |
| 4,068,658 | 1/1978 | Berman. | |
| 4,069,820 | 1/1978 | Berman. | |
| 4,256,099 | 3/1981 | Dryden. | |
| 4,497,318 | 2/1985 | Donmichael. | |
| 4,580,556 | 4/1986 | Kondur. | |
| 4,848,331 | 7/1989 | Northway-Meyer | 128/200.26 |
| 5,197,463 | 3/1993 | Jeshuran. | |
| 5,203,320 | 4/1993 | Augustine | 128/200.26 |
| 5,339,805 | 8/1994 | Parker | 128/200.26 |
| 5,339,808 | 8/1994 | Don Michael | 128/200.26 |
| 5,348,000 | 9/1994 | Teves | 128/205.25 |

*Primary Examiner*—V. Millin
*Assistant Examiner*—William J. Deane, Jr.
*Attorney, Agent, or Firm*—Dorr, Carson, Sloan & Birney, P.C.

[57] ABSTRACT

An endotracheal tube can be inserted into a patient's trachea during resuscitation by using a face mask and a curved guide. The guide is inserted through a flexible port in the face mask and has a curved distal portion that extends into the patient's mouth and hypopharynx. The patient is initially resuscitated by supplying a flow of air/oxygen through the mask. An endotracheal tube is inserted over the distal end of a fiber optic probe. Resuscitation, oxygenation, or artificial ventilation continue without interruption while the fiber optic probe and endotracheal tube are inserted through a flexible port at the proximal end of the curve guide and then advanced along the guide into the patient's airway. The direction of the distal tip of the fiber optic probe can be controlled by the physician. This allows the physician to carefully guide the fiber optic probe and endotracheal tube to a position past the larynx while resuscitation continues. The fiber optic probe is then removed from within the endotracheal tube and the mask is removed while leaving the endotracheal tube in place within the trachea. The cuff on the endotracheal tube is inflated and a ventilator is connected to the proximal end of the endotracheal tube to ventilate the patient. Alternatively, the patient can be manually ventilated by connecting a resuscitation bag to the proximal end of the endotracheal tube.

17 Claims, 8 Drawing Sheets

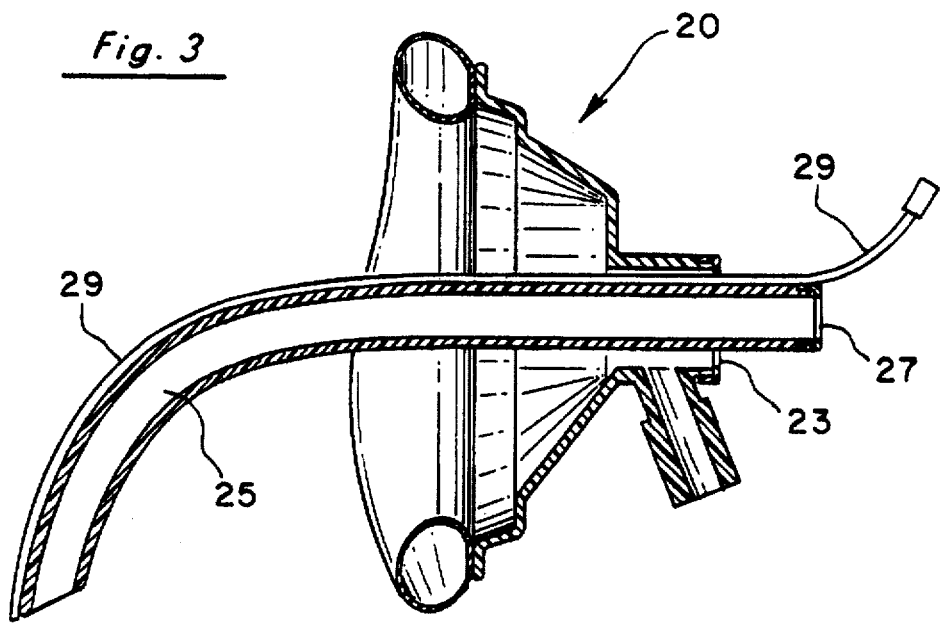
Fig. 3
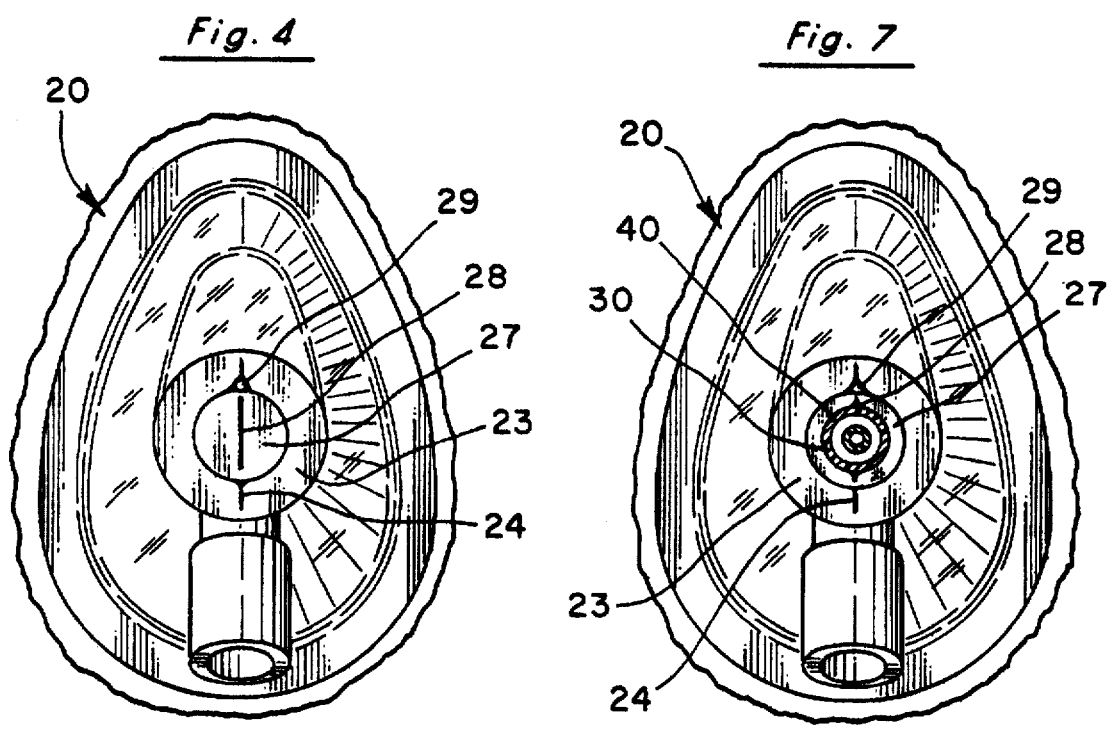
Fig. 4
Fig. 7

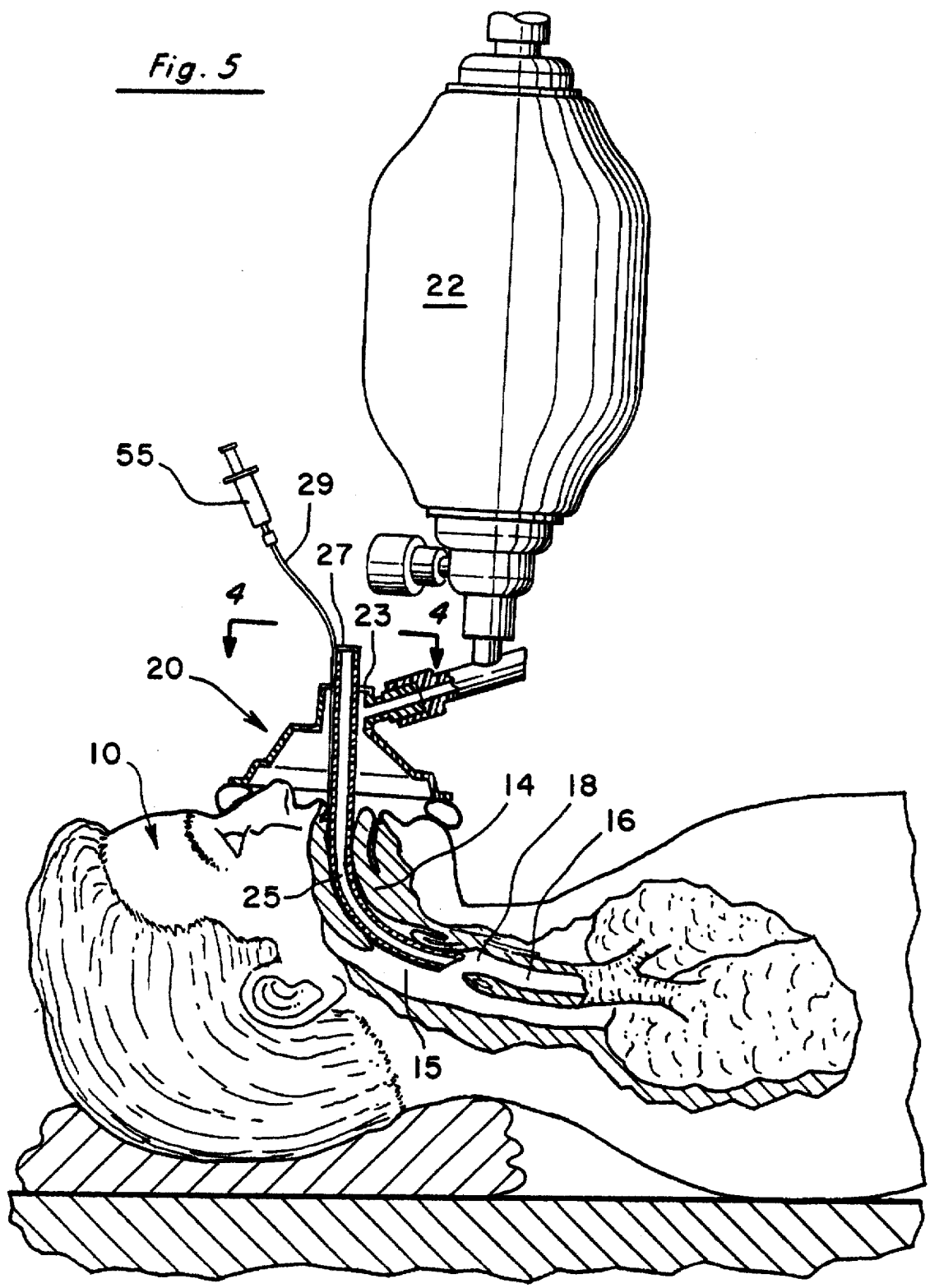

METHOD AND APPARATUS FOR VENTILATION/OXYGENATION DURING GUIDED INSERTION OF AN ENDOTRACHEAL TUBE

BACKGROUND OF THE INVENTION

1. Field of the Invention

The present invention relates generally to the field of respiratory devices and methods. More specifically, the present invention discloses a method and apparatus for guiding insertion of an endotracheal tube while the patient continues to receive cardiopulmonary resuscitation.

2. Statement of the Problem

In emergency situations involving cardiopulmonary patients or other patients with compromised or arrested breathing, an oral airway is first inserted into the patient's mouth. A face mask is then placed over the patient's mouth and nose. The face mask is connected to an inflatable bag to maintain at least minimal oxygen flow to the lungs in the short term. This process is sometimes referred to as "bagging" the patient. It is suitable for initially stabilizing the patient. In order to breathe more effectively for the patient during cardiopulmonary resuscitation, and to prevent aspiration of stomach contents, an endotracheal tube (or ET tube) is placed into the trachea. Longer-term care usually requires attaching the patient to a ventilator (e.g., by means of the endotracheal tube). The transition from face mask to breathing through the endotracheal tube can be dangerous if insertion of the endotracheal tube takes too long, because the mask and oral airway must be removed and the flow of air/oxygen is interrupted while the endotracheal tube is inserted through the patient's mouth.

The typical conventional approach to making this transition involves discontinuing resuscitation and completely removing the mask and oral airway to expose the mouth. The physician inserts a rigid laryngoscope blade into the patient's mouth to ensure that the patient's airway is open, and then attempts to insert the endotracheal tube through the patient's mouth and into the trachea in the conventional manner. This may require a significant amount of time, particularly if the patient is less than completely cooperative and relaxed, or if the patient's airway has suffered trauma, or the tongue has fallen back to close the airway. The patient may not be breathing during this time, or may not be breathing sufficiently to maintain adequate blood oxygen levels. If the transition process takes more than a few seconds, the physician must temporarily abandon the effort and return to resuscitation by reinserting the oral airway and replacing the face mask. The transition process may have to be repeated several times before the endotracheal tube is successfully installed. In addition, the speed with which the transition process must be completed increases the chances of a mistake being made or unnecessary injury to the patient during the intubation procedure.

Endotracheal tubes are also used in semi-emergency situations to ventilate patients with respiratory failure who may be conscious or semi-conscious. The conventional approach requires the patient to lie still while the physician inserts a rigid laryngoscope blade into the patient's mouth and trachea. Delivery of ventilation and/or oxygen is also interrupted during this period. The endotracheal tube is then inserted into place while the laryngoscope blade keeps the patient's airway open. Successful intubation depends on the patient being cooperative and completely relaxed, which unfortunately is often not the case. Even with a cooperative patient, intubation is very uncomfortable and can cause the patient to panic due to the difficulty in breathing during the procedure. This procedure can also result in a choking or gagging response that can cause the patient to regurgitate and aspirate contents from the stomach. One conventional response to these shortcomings has been to sedate the patient during intubation. Tranquilizers make the patient more cooperative and less likely to choke during intubation, but also tend to suppress the patient's breathing and blood pressure. These side effects may be unacceptable when dealing with a patient who already suffers from shallow or irregular breathing or depressed blood pressure. Therefore, a need exists for an improved device to guide insertion of an endotracheal tube and ensure that the patient's airway is open, and that also allows the patient to continue to receive air/oxygen during the insertion process.

A wide variety of devices that combine face masks with tubes for ventilation (e.g., endotracheal tubes) have been used in the past, including the following:

| Inventor | Patent No. | Issue Date |
| --- | --- | --- |
| Jeshuran | 5,197,463 | Mar. 20, 1993 |
| Kondur | 4,580,556 | Apr. 8, 1986 |
| Donmichael | 4,497,318 | Feb. 5, 1985 |
| Dryden | 4,256,099 | Mar. 17, 1981 |
| Buttaravoli | 3,809,079 | May 7, 1974 |

Jeshuran shows an anesthesia mask 28 that is initially placed over the patient's mouth and nose as shown in FIG. 7 of the Jeshuran patent. A fiber optic 40 is inserted through an endotracheal tube, and then through an opening in a two-piece core 84, 86, as shown in FIG. 9. The fiber optic 40 is advanced into the trachea. The head 96 is then unscrewed and the core segments 84, 86 are disassembled to allow the endotracheal tube to be inserted through the mask, as shown in FIG. 2. The fiber optic 40 serves as a guide for insertion of the endotracheal tube 46. The fiber optic 40 is then withdrawn and the endotracheal tube cuff 136 is inflated, as shown in FIG. 8. However, Jeshuran does not show a curved guide to direct insertion of the fiber optic probe. The physician is faced with the problem of navigating the fiber optic probe past the patient's tongue and along the patient's airway.

Kondur discloses another example of a adapter 10 that allows insertion of an endotracheal tube 40 through the face mask 50 and nose of the patient. Here again, no curved guide is provided.

Donmichael discloses an esophageal obturator for blocking aspiration of stomach fluids while the face mask is being used for ventilating the lungs.

Dryden discloses a two-tube resuscitation system. One tube is used to supply air to the trachea, while the other tube is used for aspiration or administering medication.

Buttaravoli discloses a resuscitator having a face mask 11 with a curved tube 15 for supplying air to the patient's airway.

In addition, the prior art includes several references involving intubating pharyngeal airways that have a curved central tubular member, including the following:

| Inventor | Patent No. | Issue Date |
| --- | --- | --- |
| Berman | 4,054,135 | Oct. 18, 1977 |
| Berman | 4,067,331 | Jan. 10, 1978 |

| Inventor | Patent No. | Issue Date |
| --- | --- | --- |
| Berman | 4,068,658 | Jan. 17, 1978 |
| Berman | 4,069,820 | Jan. 24, 1978 |

The Berman patents show an intubating pharyngeal airway having a side access for passage of a tube. The side opening can be expanded or closed by means of either a hinge on the opposite side wall of the tube or by a cap.

3. Solution to the Problem

None of the prior art references uncovered in the search show a face mask that incorporates a port and a curved guide for directing a fiber optic probe and endotracheal tube along the patient's airway while resuscitation, cardiopulmonary resuscitation, artificial mask breathing, or oxygenation continues. After the distal end of the fiber optic probe has guided the endotracheal tube past the larynx into the trachea, the fiber optic probe is withdrawn and the endotracheal tube can be used to more effectively "bag" the patient, or the patient can be connected to an external ventilator.

This system allows the endotracheal tube to be inserted and connected to a ventilator without interrupting resuscitation or oxygenation of the patient via the face mask. In addition, the curved guide greatly simplifies insertion of the fiber optic probe and endotracheal tube by providing direction and maintaining an open passageway past the patient's tongue and into the hypopharynx. The flow of air/oxygen supplied by the resuscitation bag tends to inflate the patient's mouth and airway, and thus also helps to maintain a passageway and visualization for the fiber optic probe and endotracheal tube.

SUMMARY OF THE INVENTION

This invention provides a method and apparatus for guiding insertion of an endotracheal tube into a patient's trachea during resuscitation by using a face mask and a curved guide. The guide is inserted through a flexible port in the face mask and has a curved distal portion that extends into the patient's mouth and hypopharynx. The patient is initially resuscitated by supplying a flow of air/oxygen through the mask. An endotracheal tube is inserted over the distal end of a fiber optic probe. Resuscitation, oxygenation, or artificial ventilation continue without interruption while the fiber optic probe and endotracheal tube are inserted through a flexible port at the proximal end of the guide and then advanced along the guide into the patient's airway. The direction of the distal tip of the fiber optic probe can be controlled by the physician. This allows the physician to carefully guide the fiber optic probe and endotracheal tube to a position past the larynx while resuscitation continues. The fiber optic probe is then removed from within the endotracheal tube and the mask is removed while leaving the endotracheal tube in place within the trachea. The cuff on the endotracheal tube is inflated and a ventilator is connected to the proximal end of the endotracheal tube to ventilate the patient. Alternatively, the patient can be manually ventilated by connecting a resuscitation bag to the proximal end of the endotracheal tube.

A primary object of the present invention is to provide a method and apparatus for guiding insertion of an endotracheal tube that does not require interruption of the resuscitation process.

Another object of the present invention is to provide a method and apparatus for improving insertion of an endotracheal tube by helping to keep the patient's airway open, and also allowing the physician to guide the insertion process via the fiber optic probe.

Another object of the present invention is to provide a method and apparatus for instilling local anesthetic into the patient's airway and suctioning excess secretions prior to insertion of the endotracheal tube.

Another object of the present invention is to provide a method and apparatus for guiding insertion of an endotracheal tube that lessens the risk of injury and reduces patient discomfort.

Yet another object of the present invention is to provide a device that enables the physician to instill anesthetic and/or suction secretions from the patient's mouth and airway as the device is inserted.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 3 is a cross-sectional view of the mask assembly corresponding to FIG. 1.

FIG. 4 is a front view of the face mask port 23 showing the elastic slot 28 closed.

FIG. 5 is a cross-sectional view of the mouth and airway of a patient after the mask 20 has been initially placed over the patient's mouth and nose with the curved guide 25 extending into the mouth, over the tongue 14, and into the hypopharynx 15.

FIG. 7 is a front view of the mask port 23 corresponding to FIG. 6 showing the fiber optic probe 30 and endotracheal tube 40 in cross-section.

DETAILED DESCRIPTION OF THE INVENTION

Figure 1:
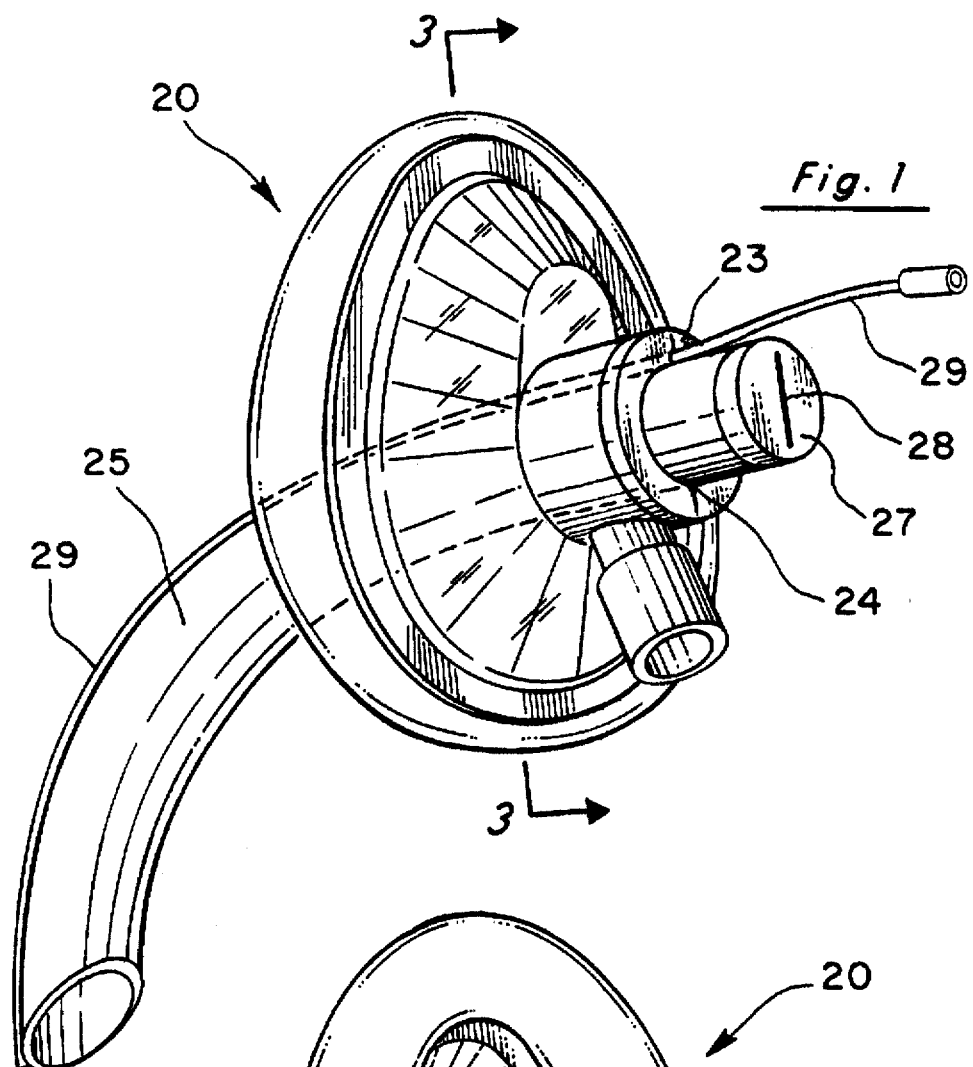
FIG. 1 is a front perspective view of the face mask assembly, including the port 23 and curved guide 25.
Figure 2:
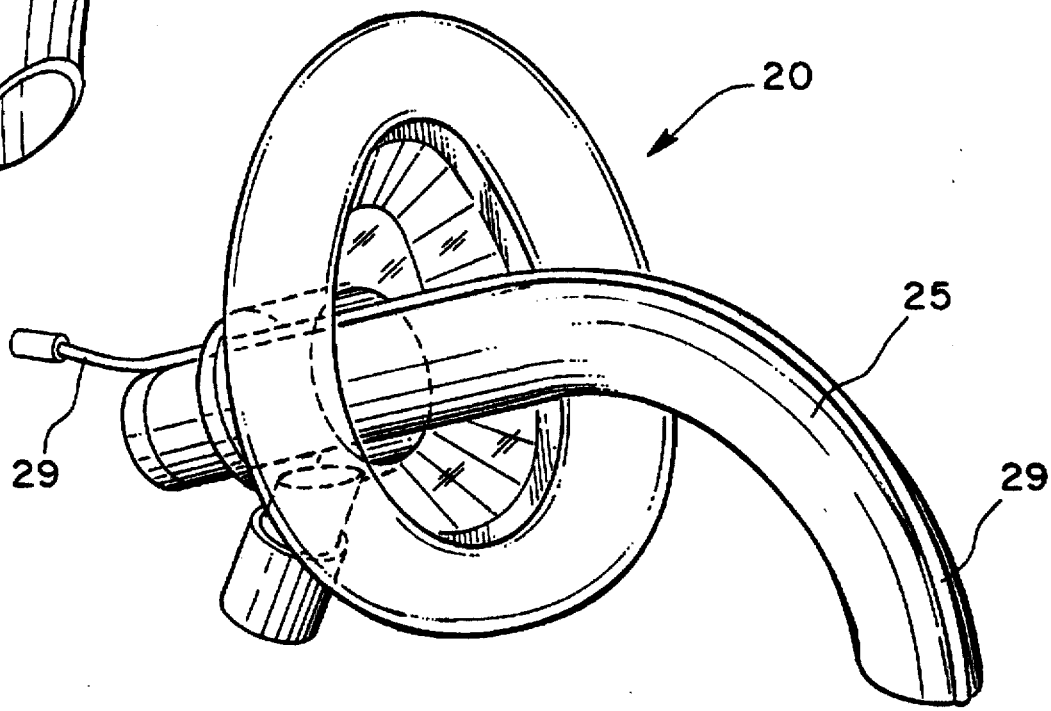
FIG. 2 is a rear perspective view of the mask assembly corresponding to FIG. 1.

Turning to FIGS. 1 and 2, front and rear perspective views of the present invention are illustrated. A corresponding cross-sectional view is shown in FIG. 3. The face mask 20 is adapted to fit over the patient's mouth and nose for resuscitation of the patient 10 as shown in FIG. 5. The mask 20 has a low profile and is made of an elastic material, such as rubber or flexible plastic, to allow the mask to conform to the contours of the patient's face and create a more air-tight seal around the mouth and nose.

The face mask 20 includes a sealable port 23. In the preferred embodiment, the face mask port 23 consists of a flexible, elastic membrane having a stretchable opening 24 with dimensions large enough to allow a curved guide 25 to pass through the face mask port 23. For example, this elastic membrane can be made of rubber with slot or hole forming an opening 24, as shown in FIG. 4.

As depicted in FIG. 5, the curved guide 25 can be readily inserted through the face mask port 23 while maintaining a substantially air-tight seal around the guide 25 to prevent gas from escaping from within the face mask 20. The guide 25 is generally tubular and includes a sealable port 27 at its proximal end. For example, the guide port 27 can be made of a flexible, elastic membrane having a stretchable slot or opening 28 with dimensions large enough to allow an endotracheal tube to pass through the guide port 27. The guide 25 extends posteriorly through the face mask 20 and has a curved distal portion that is inserted into the patient's mouth and hypopharynx 15 as the face mask 20 is placed over the patient's mouth. The distal portion of the curved guide 25 generally follows the profile of a typical patient's airway through the mouth, over the tongue 14, and into the hypopharynx 15 just above the opening to the trachea 16. The guide 25 is shaped to prevent the patient's tongue 14 and collapsible pharynx from obstructing access to the trachea 16, while also defining a channel for later insertion of an endotracheal tube. The guide 25 is typically made of plastic with sufficient strength and rigidity to keep the patient's teeth apart and prevent the patient from biting down on the endotracheal tube. The face mask port 23 allows the guide 25 to slide relative to the face mask 20, and also allows a limited range of rotation of the guide 25. This flexibility allows the guide 25 to accommodate a wide range of patient sizes and conditions.

In the preferred embodiment, the guide 25 is equipped with small tube 29 bonded to the exterior of the guide 25 that extends along the length of the guide 25 to its distal end. This tube 29 can be used to suction secretions from the patient's mouth and airway as the guide 25 is advanced. Alternatively a syringe 55 containing a local anesthetic (e.g., lidocaine or xylocaine) can be connected to the proximal end of the tube 29 to squirt anesthetic as the guide 25 is insert through the patient's mouth and into the hypopharynx 15, as illustrated in FIG. 5. If squirted with sufficient force, the anesthetic can be carried as far as the larynx 18 to deaden any discomfort associated with insertion of the endotracheal tube 40. Alternatively, the physician can squirt anesthetic directly down the main passageway of the guide 25. The main passageway can also be used for suctioning secretions from the patient's mouth and airway.

The patient is initially resuscitated by supplying a flow of air/oxygen through the mask. For example, the flow of air can be supplied by a resuscitation bag 22 attached to the mask 20 that is manually squeezed periodically to simulate natural breathing. However, other conventional air/oxygen supplies for resuscitation could be substituted at the connector 23 for the face mask 20. In the preferred embodiment, the flow of oxygen/air from the resuscitation bag 22 is directed around the exterior of the curved guide 25. This tends to inflate the patient's mouth and airway, which distends the collapsible tissues, and thereby makes visualization and insertion of the endotracheal tube 40 easier.

Figure 6:
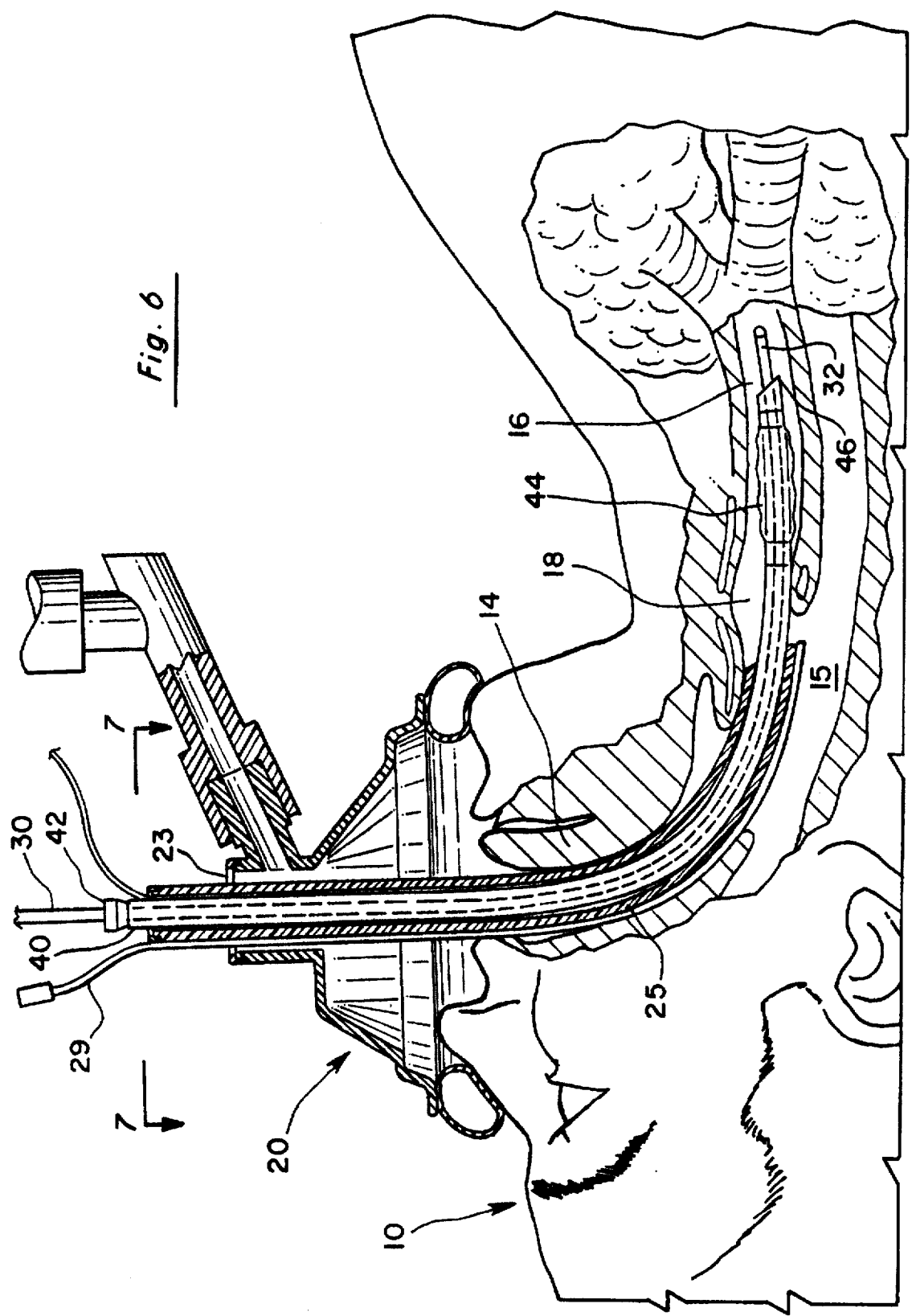
FIG. 6 is a cross-sectional view of the mouth and airway of the patient corresponding to FIG. 5 after the fiber optic probe 30 and endotracheal tube 40 have been inserted through the face mask port 23 and advanced along the curved guide 25 to a position below the larynx 18.

After the patient's conditioned has been stabilized to some degree during initial resuscitation, an endotracheal tube 40 is inserted over a fiber optic probe 30. The fiber optic probe 30 and endotracheal tube 40 are then inserted through the guide port 27 and along the guide 25 to a position within the trachea 16 past the larynx 18 while resuscitation continues, as illustrated in FIG. 6. The opening 28 in the flexible membrane stretches to allow the endotracheal tube 40 and fiber optic probe 30 to pass through the guide port 27, but maintains a sufficiently tight fit around the endotracheal tube 40 to prevent the escape of gas from within the mask 20, as shown in the front view of the face mask provided in FIG. 7.

The fiber optic probe 30 allows the physician to view within the patient's mouth and trachea 16 during insertion. The physician can also remotely manipulate the direction of the probe tip 32 to control the direction of the fiber optic probe 30. This minimizes patient discomfort and risk of injury to the patient. The small size of the fiber optic probe 30 also allows the physician to thread the fiber optic probe 30 through relatively constricted areas within the airway, such as the larynx 18. Most importantly, the fiber optic probe 30 and endotracheal tube 40 do not interfere with ongoing resuscitation of the patient.

The distal end 46 of the endotracheal tube 40 can beveled as illustrated most clearly in FIG. 6. Experience has shown that injury to the larynx 18 can be reduced by spinning the endotracheal tube 40 as it is advanced. The beveled end tends to keep the endotracheal tube 40 centered as it is passes through the vocal cords. Injury to the lining of the mouth and trachea can be reduced by using an endotracheal tube 40 made of a material having a low coefficient of friction, such as silicone. Bivona Medical Technologies of Gary, Ind., markets a line of endotracheal tubes made of silicone with a helical reinforcing wire.

Figure 8:
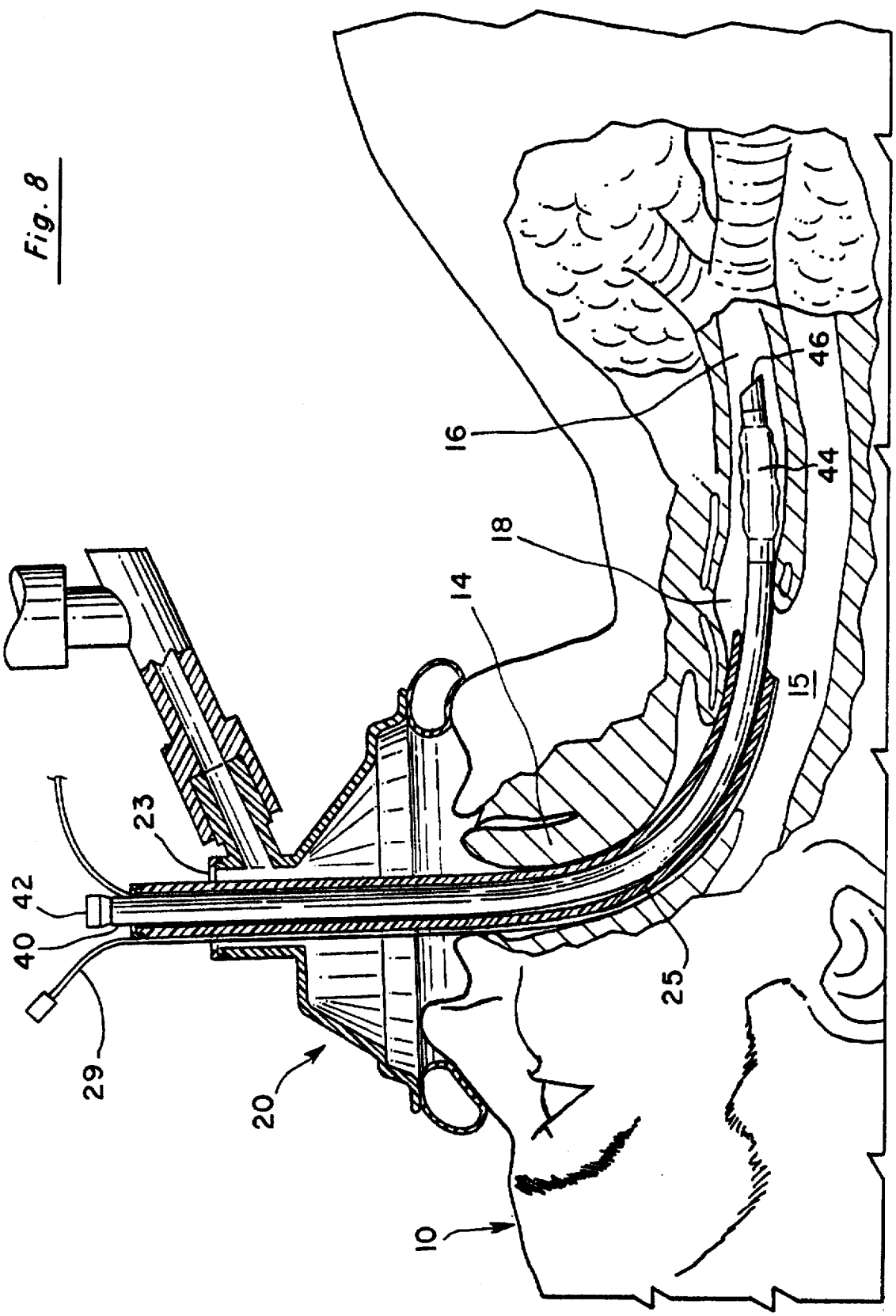
FIG. 8 is a cross-sectional view of the mouth and airway of the patient corresponding to FIG. 5 after the fiber optic probe 30 has been removed from within the endotracheal tube 40.
Figure 9:
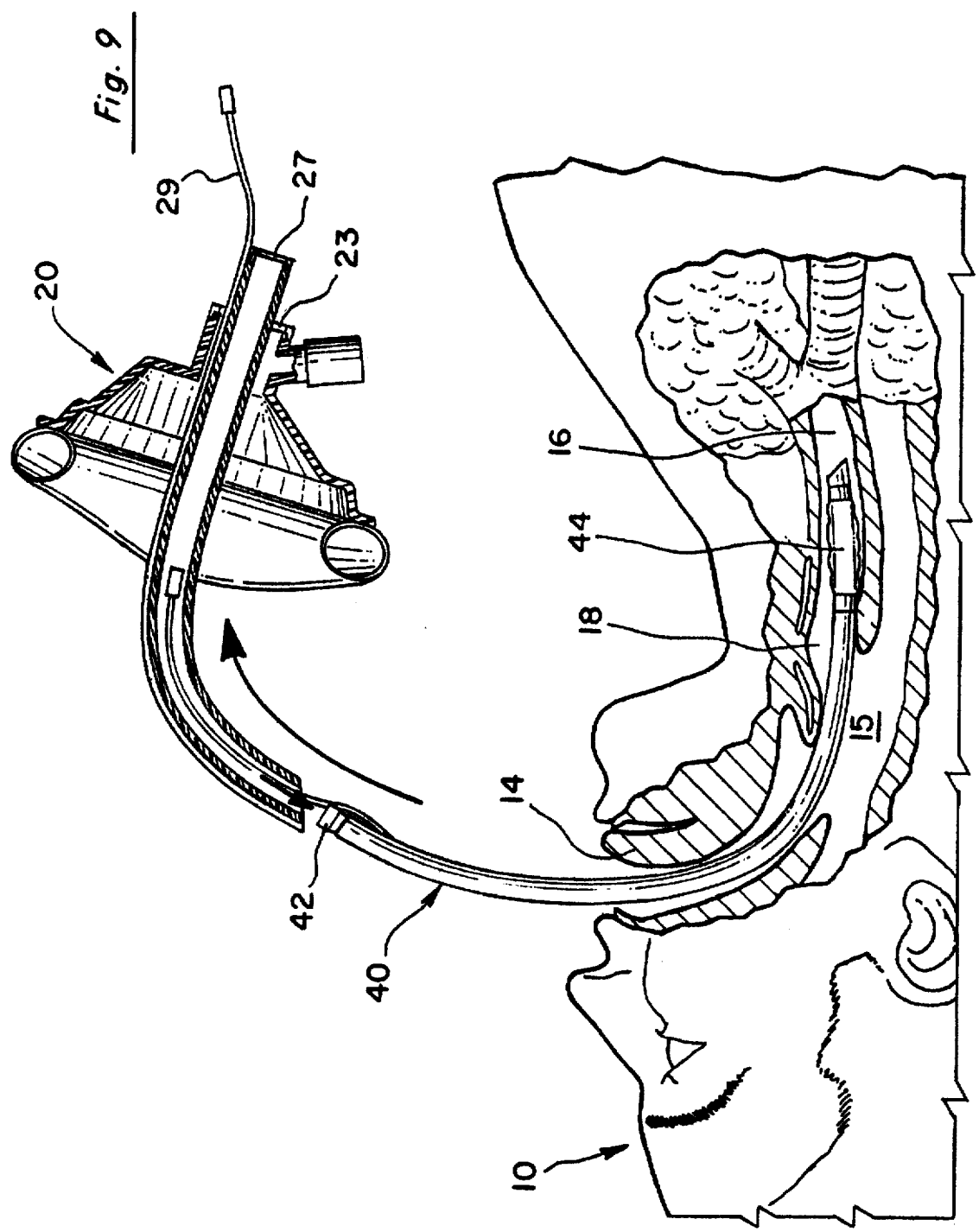
FIG. 9 is a cross-sectional view of the mouth and airway of the patient corresponding to FIG. 5 showing the face mask 20 being removed while the endotracheal tube 40 remains in place.

After the endotracheal tube 40 has been inserted, the fiber optic probe 30 is removed from within the endotracheal tube 40 through the proximal end of the endotracheal tube 40, as depicted in FIG. 8. The face mask 20 and guide 25 can then be removed while leaving the endotracheal tube 40 in place within the trachea 16, as shown in FIG. 9. The opening 28 in the flexible port 27 allows the face mask 20 and guide 25 to be withdrawn over the connector 42 at the proximal end of the endotracheal tube 40 with minimal effort and dislocation of the endotracheal tube 40. The position of the endotracheal tube 40 can be stabilized while the mask 20 is removed by manually gripping the proximal end of the endotracheal tube 40 and gradually urging it through the port 27 as the mask 20 is lifted from the patient's face. The physician can then reach under the face mask 20 to grip the endotracheal tube 40 after the mask 20 has been lifted sufficiently to allow access.

Alternatively, the face mask 20 can be removed while leaving the guide 25 in place to serve as an oral airway and to protect the endotracheal tube 40 from being bitten by the patient's teeth. After the face mask 20 has been removed, the endotracheal tube is taped to the patient's face, or held in place by some other suitable means for attachment.

Figure 10:
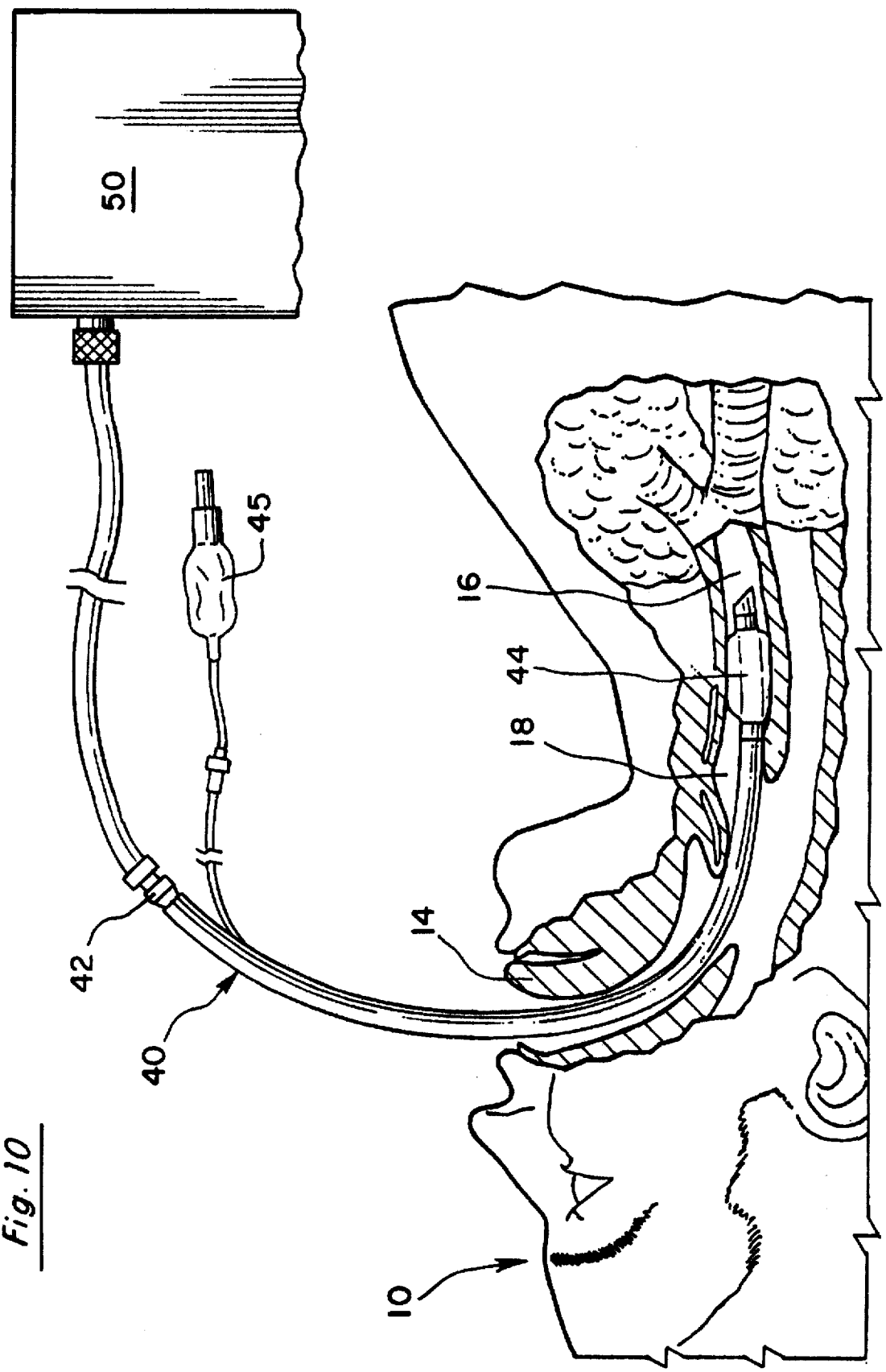
FIG. 10 is a cross-sectional view of the mouth and airway of the patient corresponding to FIG. 5 after the mask 20 has been removed, the endotracheal tube cuff 44 has been inflated, and a ventilator 50 has been connected to the endotracheal tube 40.

The cuff 44 at the distal end 46 of the endotracheal tube 40 is then inflated through the port valve 45 to block the trachea 16. An external ventilator 50 can be attached to the connector 42 at the proximal end of the endotracheal tube 40, as shown in FIG. 10. The patient can then be mechanically ventilated in the conventional manner via the endotracheal tube 40. Alternatively, the patient can be manually ventilated by attaching a resuscitation bag to the connector 42 at the proximal end of the endotracheal tube.

Figure 11:
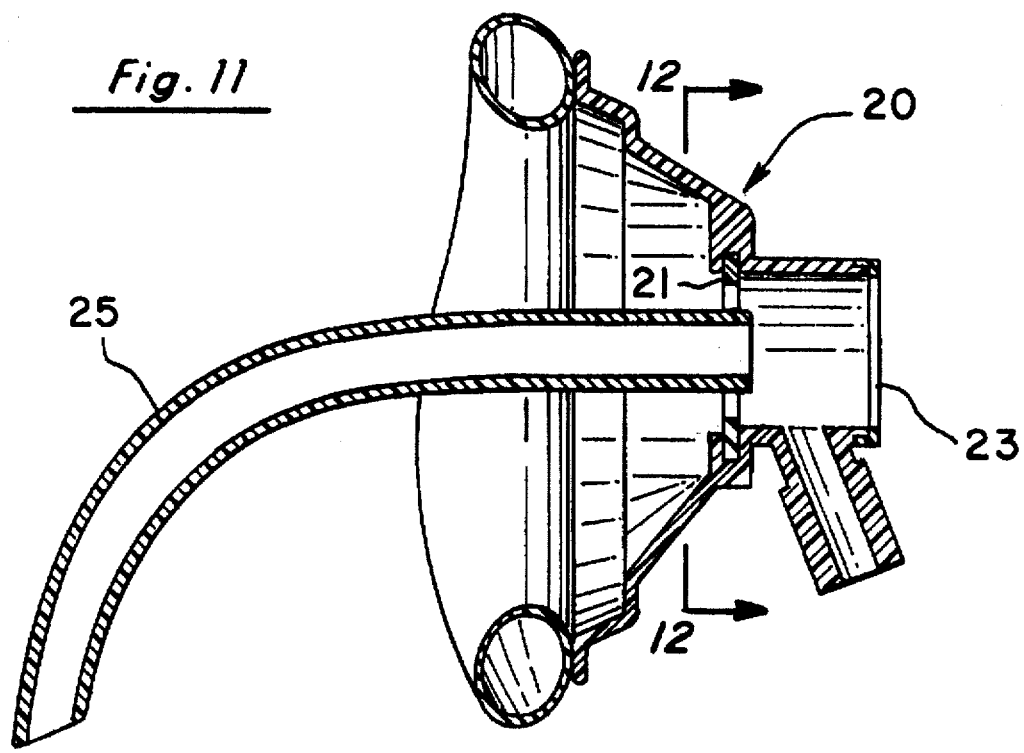
FIG. 11 is a cross-sectional view of the face mask 20 and guide 25 in an alternative embodiment in which the curved guide 25 is configured as a oral airway that engages the posterior surface of the mask 20 surrounding the face mask port 23.
Figure 12:
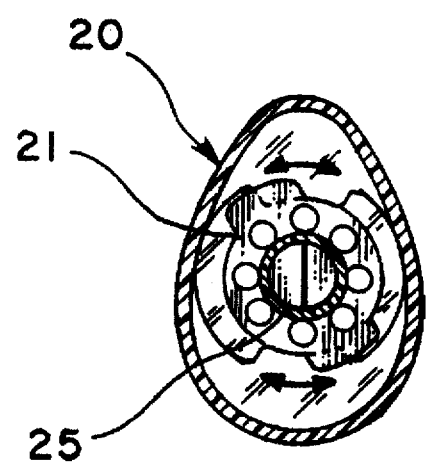
FIG. 12 is a rear detail view of locking mechanism 21 used to engage the curved guide 25 to the posterior surface of the mask 20.

It should be understood that the guide 25 and mask 20 can have any number of possible embodiments. The embodiment shown in the drawings uses a guide 25 that extends through an elastic port 23 in the face mask 20. This allows a limited range of motion between the guide 25 and mask 20 to make insertion of the guide easier, but requires two elastic ports 23 and 28. Alternatively, the guide 25 and mask 20 could be fabricated as two separate pieces that engage one another, as illustrated in FIG. 11. This eliminates the need for the guide port 27. In this embodiment, the guide 25 is separately inserted into the mouth, similar to a conventional oral airway. The mask 20 is then placed over the patient's mouth and nose so that the proximal end of the guide 25 engages a corresponding opening in the posterior face of the mask 20 to provide a relatively continuous passageway for insertion of the fiber optic probe 30 and endotracheal tube 40 through the face mask port 23 and along the guide 25. FIG. 12 provides a rear detail view of the locking mechanism 21 used to engage the guide 25 to the posterior face of the mask 20. The guide 25 can be readily disengaged by rotating it slightly relative to the face mask 20. After the endotracheal tube 40 has been inserted, the mask 20 is removed while leaving the guide 25 in place within the patient's mouth. The guide 25 remains around the endotracheal tube 40 and protects it from being bitten or crimped by the patient's teeth.

The guide 25 can consist of a tubular member as shown in the drawings. Alternatively, the distal portion of the guide 25 can have a U-shaped cross-section. The guide 25 can be molded from a suitable plastic material having a relatively low coefficient of friction to minimize irritation to the lining of mouth and trachea and to minimize resistance to insertion of the endotracheal tube 40 along the guide. Friction can be further reduced by applying a slippery coating to both the exterior and interior surfaces of the guide 25. A slippery coating can also be applied to the endotracheal tube to minimize friction between the endotracheal tube and the guide.

All of the components necessary to practice the present invention can be readily packaged as a kit for use in emergency rooms and intensive care units. The kit is sufficiently compact and inexpensive that it can be stocked on resuscitation carts widely used in hospitals, and carried in ambulances for use by emergency medical technicians in the field. The fiber optic probe can be operated using a battery-powered light source. The oxygen supply for the hospital or ambulance can be connected to the face mask 20 for resuscitation or to provide a flow of gas to the ventilator 50. The tube 29 extending along the guide 29 can also be connected to the suction system provided by the hospital or ambulance, if necessary.

The above disclosure sets forth a number of embodiments of the present invention. Other arrangements or embodiments, not precisely set forth, could be practiced under the teachings of the present invention and as set forth in the following claims.

I claim:

1. An apparatus for guiding insertion of an endotracheal tube into the trachea of a patient, said comprising:
   a face mask for covering said patient's mouth;
   means for supplying a flow of air/oxygen into said mask to resuscitate said patient;
   a sealable face mask port; and
   a guide extending through said face mask port having:
      (a) a curved distal portion for insertion into said patient's mouth and hypopharynx; said guide directing insertion of an endotracheal tube into said patient's trachea; and
      (b) a sealable guide port allowing removable insertion of the endotracheal tube along said guide.

2. The apparatus of claim 1 wherein said port comprises a flexible membrane having a stretchable opening for receiving said endotracheal tube.

3. The apparatus of claim 1 wherein said guide comprises a tube having a curved distal portion.

4. The apparatus of claim I wherein said means for supplying a flow of air/oxygen to said mask comprises a resuscitation bag attached to said mask.

5. The apparatus of claim 1 wherein said flow of air/oxygen is directed around the exterior of said guide.

6. A method for guiding insertion of an endotracheal tube into a patient's trachea comprising:
   placing a mask over said patient's mouth, said mask having a guide extending posteriorly from said mask with a sealable port for allowing removable insertion of said endotracheal tube through said mask and a curved distal portion inserted into said patient's mouth and hypopharynx;
   resuscitating said patient by supplying a flow of air/oxygen through said mask;
   inserting a fiber optic probe through an endotracheal tube;
   advancing said fiber optic probe and endotracheal tube through said port and along said guide into said patient's trachea while resuscitation continues;
   removing said fiber optic probe through said port;
   removing said mask while leaving said endotracheal tube in place within said patient's trachea; and
   ventilating said patient through said endotracheal tube.

7. The method of claim 6 wherein said fiber optic probe is inserted to a position beyond said patient's larynx.

8. The method of claim 6 wherein said port comprises a flexible membrane having a stretchable opening for receiving said fiber optic probe and endotracheal tube.

9. The method of claim 6 wherein said guide comprises a tube having said port at its proximal end and a curved distal portion.

10. The method of claim 6 wherein said guide has a substantially U-shaped cross-section.

11. The method of claim 6 wherein said face mask further comprises a sealable face mask port having a stretchable opening for receiving said guide.

12. A method for guiding insertion of an endotracheal tube into a patient's trachea comprising:
   placing a mask over said patient's mouth, said mask having a guide extending posteriorly from said mask with a sealable port for allowing removable insertion of said endotracheal tube through said mask, and a curved distal portion inserted into said patient's mouth and hypopharynx;
   resuscitating said patient by supplying a flow of air/oxygen through said mask;
   inserting a fiber optic probe through said endotracheal tube;
   inserting said fiber optic probe and endotracheal tube through said port, along said guide, and into said patient's trachea while resuscitation continues;

removing said fiber optic probe from within said endotracheal tube;

removing said mask while leaving said endotracheal tube in place within said patient's trachea; and ventilating said patient through said endotracheal tube.

13. The method of claim 12 wherein said port comprises a flexible membrane having a stretchable opening for receiving said endotracheal tube.

14. The method of claim 12 wherein said guide comprises a tube having a curved distal portion.

15. The method of claim 12 wherein said guide has a substantially U-shaped cross-section.

16. The method of claim 12 wherein said face mask further comprises a sealable face mask port having a stretchable opening for receiving said guide.

17. The method of claim 12 wherein said flow of oxygen/air is directed around the exterior of said guide.

\* \* \* \* \*